United States Patent [19]

Gulya et al.

[11] Patent Number: 4,991,425
[45] Date of Patent: Feb. 12, 1991

[54] PORTABLE GAUGE FOR MEASURING AIR FLOW IN A PAPERMAKING MACHINE

[75] Inventors: Thomas G. Gulya, Appleton; Gary V. Schultz, Kimberley, both of Wis.

[73] Assignee: Appleton Mills, Appleton, Wis.

[21] Appl. No.: 481,210

[22] Filed: Feb. 20, 1990

[51] Int. Cl.$^5$ ............................................. G01N 15/08
[52] U.S. Cl. ...................................... 73/38; 73/37.7; 15/401; 162/263
[58] Field of Search ............ 73/38, 37.7, 37.6, 861.85; 15/401, 344, 347; 162/263, 198

[56] References Cited

U.S. PATENT DOCUMENTS

| | | | |
|---|---|---|---|
| 1,446,854 | 2/1923 | Marshall | 15/401 |
| 4,311,037 | 1/1982 | Gotchel et al. | 73/38 |
| 4,401,147 | 8/1983 | Beck et al. | 73/861.85 X |
| 4,730,481 | 3/1988 | Schlipf | 73/38 |
| 4,756,183 | 7/1988 | Rajala et al. | 73/38 |
| 4,905,500 | 3/1990 | Mason | 73/38 |

*Primary Examiner*—Hezron E. Williams
*Assistant Examiner*—Joseph W. Roskos
*Attorney, Agent, or Firm*—Andrus, Sceales, Starke & Sawall

[57] ABSTRACT

An apparatus for measuring air permeability and boundary air flow for a papermaking fabric, such as a dryer felt. The apparatus includes a housing having an open front end bordered by a lower straight edge. An air flow measuring device, such as an anemometer is mounted in the rear surface of the housing a funnel-shaped deflector directs air entering the open front end of the housing to the anemometer. Air flowing through the anemometer generates an electrical signal in proportion to air flow. The electrical signal actuates a visual display mounted on the housing which provides a visual indication of air flow. A thin blade is mounted at the open front edge of the housing and is adapted to ride along the moving fabric when the apparatus is used. A handle is secured to the upper surface of the housing and extends forwardly of the front end and is adapted to be grasped by an operator.

15 Claims, 1 Drawing Sheet

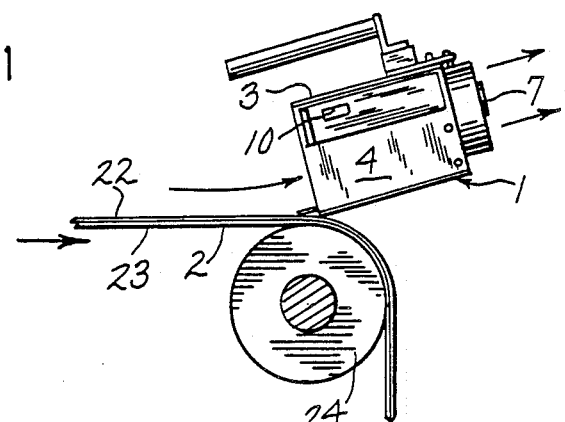
FIG. 1
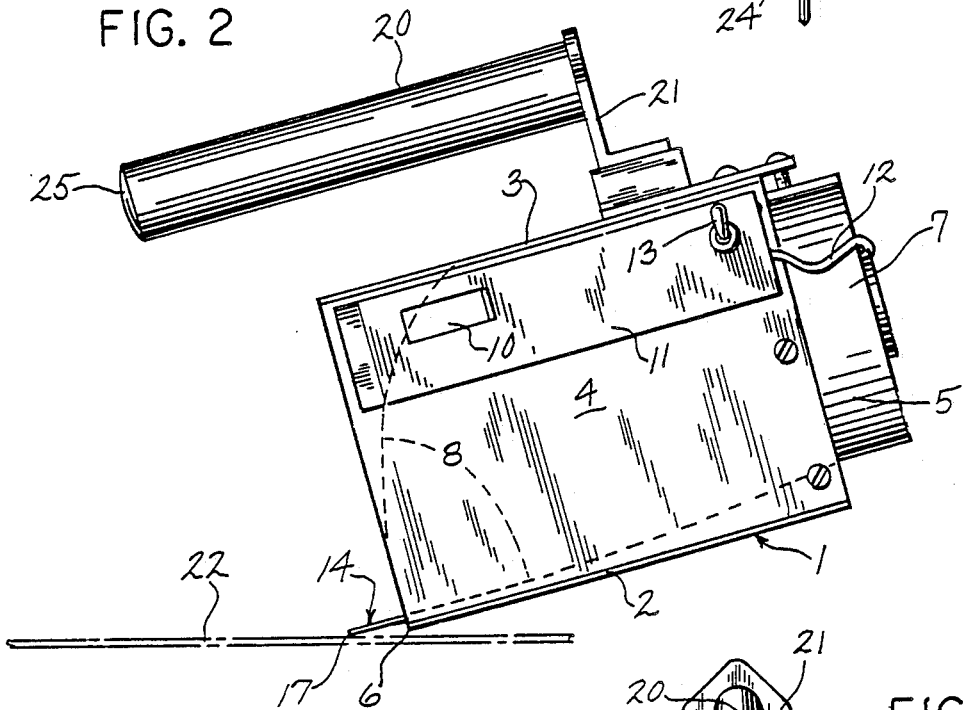
FIG. 2
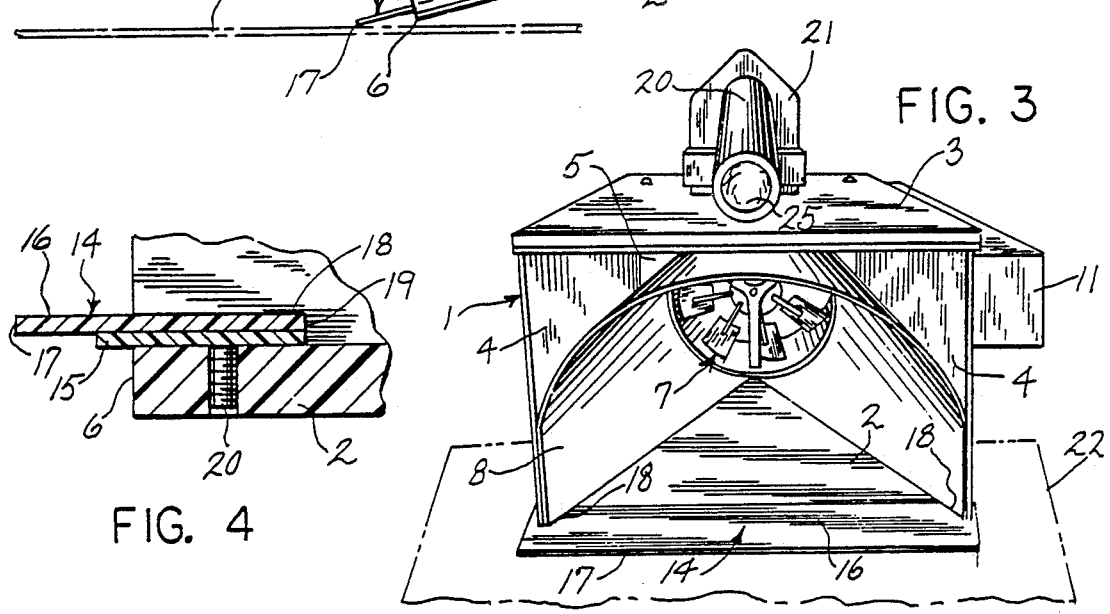
FIG. 3
FIG. 4

PORTABLE GAUGE FOR MEASURING AIR FLOW IN A PAPERMAKING MACHINE

BACKGROUND OF THE INVENTION

In the dryer section of a papermaking machine, the paper sheet or web is carried over a series of heated dryer drums by a dryer felt. The dryer felt is generally fabricated from woven synthetic materials and depending upon the nature of the paper sheet, the dryer felt can have different surface smoothness and air permeability. When drying coarser material, such as liner board, paperboard, or corrugated medium, a coarse or rough surface dryer felt is normally utilized having high air permeability. A dryer felt of this type provides maximum air pumping to achieve a high drying rate. With other types of paper, a fine, smooth surface dryer felt may be employed having low air permeability which reduces air pumping and minimizes fluttering of the sheet. Thus, the surface smoothness and air permeability of the dryer felt must be balanced with the characteristics of the paper sheet to obtain maximum drying without excessive sheet fluttering.

The surface smoothness of the dryer felt determines the rate of boundary air, which is the air carried on the surface of the fabric. As the surface roughness of the felt is increased, the rate of flow of the boundary air is correspondingly increased.

Flutter of the paper sheet can occur when the sheet is picked up on the dryer drum and is attributable to the boundary air, meaning the greater the flow of boundary air, the greater the tendency for flutter. Flutter can also occur at a converging nip where the dryer felt carrying the paper sheet approaches the dryer drum and the air in the converging space is forced outwardly through the felt to cause flutter of the paper sheet carried on the outer surface of the felt. Excessive flutter can cause breakage of the paper sheet and downtime of the papermaking machine. In view of this, it is important to be able to measure the boundary air characteristics of dryer felts to thus determine the propensity of the felt for flutter.

During service, the dryer felt will tend to clog with resin and foreign material, resulting in a decrease in air permeability and a corresponding decrease in the drying rate. A papermaking machine is intended to run continuously 24 hours per day and seven days per week. In the past there has been no mechanism for determining the air permeability of a dryer felt while the papermaking machine is in operation. It has only been in instances where the machine has been shut down for maintenance that a measurement of the air permeability could be made on the stationary dryer felt. Thus, there has been a need for a device which is capable of measuring air permeability, while the papermaking machine is in operation.

SUMMARY OF THE INVENTION

The invention is directed to an apparatus or gauge for measuring the air permeability and the boundary air flow of a papermaking fabric, such as a dryer felt, while the papermaking machine is in operation. In accordance with the invention, the gauge includes a housing having an open front end bordered by a lower straight edge. An air flow measuring device, such as an anemometer is mounted in the rear surface of the housing and a funnel-shaped deflector or foil interconnects the front edge of the housing with the anemometer and serves to direct or funnel air from the front end through the anemometer.

The anemometer generates an electrical signal corresponding to the air flow and the electrical signal is converted to a visual display such as an index number, corresponding to the air flow.

A thin, plastic blade is removably connected to the lower straight edge of the housing and is adapted to ride against the surface of the dryer felt or fabric during operation of the gauge. The blade serves to scrape along the fabric and doctor the air into the housing. To facilitate positioning of the gauge, a handle is secured to the upper surface of the housing and extends forwardly beyond the open front end of the housing. In use, the operator will grasp the handle and hold the blade in contact with the moving fabric or felt.

The gauge of the invention can be used to either determine air permeability or boundary air flow of a papermaking fabric and particularly a dryer felt. In use in determining air permeability, the open end of the gauge is faced upstream with respect to the direction of felt travel with the blade riding against the outer surface of the felt. The gauge is positioned adjacent to the point of tangency where the felt converges toward the dryer drum. Air within the felt, as well as the air within the converging space between the felt and the drum, is pumped through the fabric and into the housing to thereby generate an index reading of air flow. If desired, the index reading can be converted through use of a mathematical equation into air flow in cubic feet/minute or cubic meters/minute.

In using the gauge to determine boundary air flow, the gauge is positioned either along a straight run of the felt, or alternately adjacent the point of tangency where the felt diverges from the dryer drum. Again, the air is directed into the housing and through the anemometer to provide an index reading of boundary air flow.

The invention provides a portable, lightweight gauge which can be used either to determine boundary air flow or air permeability of a papermaker's fabric, while the papermaking machine is in operation.

Other object and advantages will appear in the course of the following description.

DESCRIPTION OF THE DRAWINGS

The drawings illustrate the best mode presently contemplated of carrying out the invention.

In the drawings:

FIG. 1 is a schematic representation showing the manner of use of the gauge of the invention;

FIG. 2 is a side elevation of the gauge;

FIG. 3 is a front perspective view of the gauge; and

FIG. 4 is an enlarged fragmentary vertical section showing the attachment of the blade to the housing.

DESCRIPTION OF THE ILLUSTRATED EMBODIMENT

The drawings illustrate a portable lightweight gauge that can be used to measure the air permeability or boundary air flow of a papermaking fabric and particularly a dryer felt. The gauge includes an open ended housing 1 formed of plastic or metal and the housing includes a bottom wall 2, top wall 3, a pair of rearwardly converging side walls 4 and a rear wall 5. The front or forward edge 6 of bottom wall 5, which borders the open front end, is straight, as shown in FIG. 3.

An air flow measuring device, such as an anemometer 7 is mounted within an opening in rear wall 5. As shown, the anemometer 7 is a standard fan-type, but it is also contemplated that other types of air flow measuring devices, such as a hot wire anemometer, can also be employed.

Connecting the open front of housing 1 with anemometer 7 is a funnel-shaped foil or deflector 8. The sides of deflector 8 are secured to the forward portions of side walls 4, as shown in FIG. 3, and the upper portion 9 of the deflector is curved, while the rear portion converges inwardly and borders the opening leading to anemometer 7. Thus, air entering the front open end of the housing 1 is funneled smoothly into the anemometer 7. Alternately, housing 1 can be contoured to direct or funnel the air to anemometer 7, so that a separate deflector 8 would not be required.

The air flowing through anemometer 7 generates an electrical signal and the electrical signal operates a visual display 10 located in control box 11, which is mounted to the upper portion of one of the side walls 4. Visual display 10 can take the form of index numerals, with the higher the numeral representing a higher rate of air flow. Thus, the numerals can provide a comparative index as to the rate of air flow. If desired, the index reading can be converted to an air flow rate in cubic feet/minute or cubic meters/minute through use of a suitable mathematical equation.

Electrical leads 12 connect the anemometer with the visual display 10 in the control box, and an on-off switch 13 is mounted on control box 11 and controls the operation of the display.

A thin, plastic blade 14 is removably mounted on front edge 6 and is adapted to ride on the surface of the dryer felt or other fabric when the gauge is being used. Blade 14 can be formed of a material, such as Mylar (polyester) and preferably has a thickness less than 0.020 inch. In its preferred form, blade 14 is formed of a pair of overlapping sections 15 and 16, which are secured flatwise together. The upper section 16 projects outwardly beyond the lower section 15 and the outer extremity or edge 17 of section 16 is adapted to ride against the dryer felt or other fabric. The lower section 15 reinforces or stiffens the upper blade section 16, which is relatively thin, having a thickness generally in the neighborhood of about 0.015 inch. During service as the edge 17 rides against the fabric, the edge will wear to a generally sharpened extremity.

Blade 14 is removably mounted with respect to housing 1. In this regard, the lower edge of each side wall 4 adjacent the open front end is provided with a front-to-rear slot 18, and the slots 18 receive the side edges of blade 14. As shown in FIG. 4, the inner end of blade 14 bears against a shoulder or abutment 19 bordering the end of the respective slot 18. One or more set screws 20, which extend through openings in bottom wall 2, can secure the blade within the slots 18. With this construction, blade 14 can be removed if damaged or worn and replaced with a new or fresh blade.

To facilitate positioning of the gauge, a tubular handle 20 is mounted on the upper surface 3 through an L-shaped bracket 21. The outer or distal end of the handle 20 projects outwardly beyond the front end of the housing 1 and the outer surface of the handle can be provided, if desired, with a cushioning layer of foam plastic. A papermaking machine may operate at high speeds up to 3,000 to 4,000 feet per minute. By positioning the handle 20 as illustrate in FIG. 2, in which the outer end of the handle extends upstream beyond the forward end of the housing, it ensures that in the event the blade 14 should engage some obstruction on the moving fabric, the housing will be thrown away from the operator's hand to prevent possible injury to the operator.

The gauge of the invention can be used to determine air permeability of a paper machine fabric, or alternately to determine boundary air flow. Its use in determining air permeability is illustrated in FIG. 1, in conjunction with the dryer section of a papermaking machine. A conventional dryer felt 22 carries a paper sheet 23 against the outer surface of a drum 24, and to determine the air permeability of the felt while the papermaking machine is in operation, the gauge is positioned, as shown in FIG. 1, with the blade 14 riding against the outer surface of felt 22. As the felt and paper 23 move toward the converging nip with drum 24, the air in the converging space, as well as the air within the felt is pumped outwardly through the felt and is doctored into the housing 1 by blade 14. The air passing through the anemometer 7 will give an indication on the visual display 10 of the air flow. With this usage, the air permeability of the felt can be measured while the machine is operating.

The outer or distal end of the handle can be provided with a button-type switch 25, which is connected to the visual display 10. By depressing the switch 25, the index reading will be held so that the operator can remove the gauge from the felt and the index reading will remain visible.

To obtain a measurement of the boundary air flow, the gauge is positioned either on a straight run of the felt 22, or alternately, it is positioned adjacent the diverging nip as the felt passes from the dryer drum 24. Again, the open end of the gauge is faced upstream in the direction of felt travel, with the blade 14 being positioned generally at the point of tangency where the felt leaves the surface of the dryer drum 24. This measurement will provide an indication of the boundary air which, in turn, is a measurement of the tendency of the sheet to flutter.

The invention provides a lightweight portable gauge which can be used to measure the boundary air flow of a papermaking fabric, or alternately, to measure the air permeability. Both measurements can be taken while the papermaking machine is in operation and thus will not necessitate any downtime for the machine.

Various modes of carrying out the invention are contemplated as being within the scope of the following claims particularly pointing out and distinctly claiming the subject matter which is regarded as the invention.

We claim:

1. An apparatus for measuring air flow in connection with a papermaking fabric, comprising housing means having an open front end and having a straight edge bordering said open front end, air flow measuring means disposed at the rear end of said housing means and having a smaller cross sectional area than said open front end for providing a measurement of air flow through said housing means, said housing means being constructed and arranged to direct air from said front end to said air flow measuring means, and a blade removably connected to said straight edge and extending forwardly of said edge, said blade being constructed and arranged to ride against said fabric and direct air into said housing.

2. The apparatus of claim 1, and including visual indicating means on the outer surface of said housing and operably connected to said air flow measuring means for providing a visual indication of the air flow.

3. The apparatus of claim 1, and including a handle connected to said housing.

4. The apparatus of claim 3, wherein said handle projects forwardly of said front end.

5. The apparatus of claim 3, wherein said housing is provided with an upper surface and said handle is secured to said upper surface and has a distal end projecting forwardly of the front end of said housing.

6. The apparatus of claim 1, wherein said housing means is provided with generally curved interior walls, leading to said air flow measuring means.

7. The apparatus of claim 1, wherein said air flow measuring means comprises an anemometer.

8. The apparatus of claim 1, wherein said blade is composed of plastic material.

9. The apparatus of claim 8, wherein said blade includes a pair of blade members disposed flatwise to each other, the end of one of said blade members projecting forwardly of the corresponding end of the other blade member and disposed to engage the fabric.

10. An apparatus for measuring air flow, comprising a housing having an open front end and having a straight edge bordering said open front end, air flow measuring means disposed at the rear end of said housing and having a smaller cross sectional area than said open front end, said measuring means providing a measurement of air flow through said housing, deflector means interconnecting the front end of said housing and said air flow measuring means for smoothly directing air from said front end to said air flow measuring means, a handle connected to said housing and having a distal end projecting forwardly of the front end of said housing, and blade means removably connected to said straight edge and extending forwardly of said edge, said blade means being constructed and arranged to ride against the outer surface of a papermaking fabric and doctor air from the fabric into said housing.

11. The apparatus of claim 10, wherein said housing is provided with a flat bottom wall and a rear wall extending normal to said bottom wall, said air flow measuring means being mounted in said rear wall.

12. The apparatus of claim 10, wherein said blade means is disposed flatwise against said bottom wall.

13. The apparatus of claim 12, wherein said blade means is disposed flatwise against the upper surface of said bottom wall.

14. The apparatus of claim 11, wherein said housing also includes a pair of side walls extending upwardly from said bottom wall, each side wall having an open-ended slot adjacent said bottom wall, the side edges of said blade means being disposed within said slots.

15. The apparatus of claim 14, and including connecting means for connecting said means to said housing.

* * * * *

UNITED STATES PATENT AND TRADEMARK OFFICE
CERTIFICATE OF CORRECTION

PATENT NO. : 4,991,425

DATED : February 12, 1991

INVENTOR(S) : THOMAS G. GULYA ET AL

It is certified that error appears in the above-identified patent and that said Letters Patent is hereby corrected as shown below:

COL. 6, LINE 28, CLAIM 15, After "said", first occurrence, insert --blade--

Signed and Sealed this

Twenty-fifth Day of August, 1992

Attest:

*Attesting Officer*

DOUGLAS B. COMER

*Acting Commissioner of Patents and Trademarks*